United States Patent [19]

Scaffidi

[11] Patent Number: 4,816,271

[45] Date of Patent: Mar. 28, 1989

[54] SKIN LOTIONS AND CREAMS

[76] Inventor: Adelia Scaffidi, 11432 W. 130th St., Strongsville, Ohio 44136

[21] Appl. No.: 4,120

[22] Filed: Jan. 16, 1987

[51] Int. Cl.$^4$ .................. A61K 7/40; A61K 7/44; A61K 9/10

[52] U.S. Cl. .................... 424/60; 514/847; 514/873; 514/938; 514/970

[58] Field of Search ............. 514/873, 847, 970, 938; 424/60

[56] References Cited

U.S. PATENT DOCUMENTS

| | | | |
|---|---|---|---|
| 3,906,108 | 9/1975 | Felty | 514/970 |
| 3,930,000 | 12/1975 | Margraf | 514/969 |
| 4,021,572 | 5/1977 | Van Scott | 514/557 |
| 4,124,720 | 11/1978 | Wenmaekers | 514/735 |
| 4,189,465 | 2/1980 | Rosenthal | 514/873 |
| 4,216,201 | 8/1980 | Calvo | 424/63 |
| 4,451,453 | 5/1984 | Lay et al. | 424/81 |
| 4,454,159 | 6/1984 | Musher | 424/358 |
| 4,505,902 | 3/1985 | Millard | 424/195.1 |
| 4,515,784 | 5/1985 | Bogardus et al. | 514/63 |
| 4,536,399 | 8/1985 | Flynn et al. | 514/63 |
| 4,595,586 | 6/1986 | Flom | 424/59 |

FOREIGN PATENT DOCUMENTS

| | | | |
|---|---|---|---|
| 0088304 | 5/1983 | Japan | 514/873 |
| 0210040 | 11/1984 | Japan | 514/970 |
| 8402271 | 6/1984 | PCT Int'l Appl. | |

OTHER PUBLICATIONS

Chem. Abs., 1983, vol. 99, p. 128152n, Kobayashi.
Chem Abs., 1984, vol. 100, p. 16168/w, Shiseido.
Chem. Abs., 1984, vol. 100, p. 161688d, Kogyo.
Merck Index, 1952, p. 966.
STN International Search Reports, CA File, Hand-numbered pp. 1–40.
Navarre, The Chemistry and Manufacture of Cosmetics, pp. 109–117, 120–123, 126–127, 134–137, 150–151.
Federal Register, vol. 43, No. 151: FDA, Skin Protectant Drug Products for Over-the -Counter Use, excerpts.
Textbook excerpt, source unknown.
Lehninger, Biochemistry, 2d ed., 1975, p. 680.
Franklin, "Shark Liver Oil", *Let's Live*, Nov. 1986, p. 60.
Author unknown, Fisheries and the Utiliziaton of Sharks, pp. 194–198.

*Primary Examiner*—Dale R. Ore
*Attorney, Agent, or Firm*—Woodling, Krost & Rust

[57] ABSTRACT

A formulation is disclosed which provides a superior moisturizer and base for cosmetics or suntan lotions. The principal active ingredient is shark liver oil.

3 Claims, No Drawings

SKIN LOTIONS AND CREAMS

This invention relates to preparations for application to the skin. More particularly, it relates to lotions and creams useful as moisturizers, bases for cosmetics, and sunburn preventives.

BACKGROUND AND SUMMARY OF THE INVENTION

Many products have been developed for the purpose of moisturizing the skin, protecting it from sunburn and providing a base into which coloring or other agents may be added for cosmetic purposes. The composition of such products commonly contains agents chosen to achieve well-defined purposes. For example, ingredients such as PABA (paraaminobenzoic acid) for sun protection, glycerin for moisturization, anti-oxidants such as alpha-tocopherol and preservatives such as methylparaben, are all well-known constituents of such preparations. The exact identities and proportions of such ingredients, however, vary because some of them may alter the effects of some others, so that it may be difficult to achieve a substantial improvement in quality of a preparation by the mere alteration or addition of a constituent.

Examples of recent prior art directed to some of these problems are U.S. Pat. Nos. 4,216,201 to Calvo; 4,454,159 to Musher, 4,505,902 to Millard and 4,595,586 to Flom.

The present invention is the result of a series of experiments designed to achieve a formulation which utilizes the benefits of shark oil (shark liver oil), a complex mixture of organic oils which has been the subject of much research in recent years. Shark oil is especially noted for its high content of squalene, a highly unsaturated terpenic hydrocarbon which is a biochemical precursor of cholesterol. Squalene, in fact, is a constituent of normal skin sebum and has been used in artificial oil and sebum preparations for testing of therapeutic products (e.g. U.S. Pat. Nos. 4,451,453 to Lay et al; 4,515,784 to Bogardus et al; and 4,536,399 to Flynn et al). Squalene or fish liver oil is also a constituent in the four earlier mentioned patents, and in various therapeutic preparations (e.g. U.S. Pat. Nos. 3,930,000 to Margraf; 4,021,572 to VanScott et al; and 4,124,720 to Wenmaekers).

The inventor herein has discovered a composition and method of formulation which permit manufacture without the use of heat to emulsify shark oil. Proportions of other ingredients have been determined also. The result is a preparation with notably superior emollient and moisturizing properties which serve both to soothe and protect the skin. Moreover, the stability of compositions made according to the present invention has proven to be more than adequate for its intended use.

DETAILED DESCRIPTION OF A PREFERRED EMBODIMENT OF THE INVENTION

The following is a detailed description of the preparation of the most effective presently known embodiment of the invention. Quantities given are for the production of about eight ounces of cream or lotion, it being of course understood that larger amounts are prepared with similar proportions of ingredients.

First six ounces of distilled water, along with a small amount of sodium chloride, about 0.09 to 0.11 weight percent of total, 1 to 2.5 ml of alcohol, or about 0.4 to 1% by weight of total, and up to about 5 ml of powdered citric acid, if desired, or 2% by weight of total, are stirred or agitated, preferably in a blender or similar device, while about six grams of gum tragacanth are added. The final tragacanth proportion by weight may vary from 2.5% to about 4%, depending on whether a lotion or a cream is desired and upon the particular brand used; 3% appears to be optimal for that obtained from Meer Products, N.Y. ("Tragacanth W") in the preferred embodiment. The water-tragacanth suspension is permitted to stand for about ten to twelve hours, until considerably thickened.

A second mixture is made as follows: 2½ grams each of glycerin and propylene glycol are combined. These function as moisturizers or humectants. The propylene glycol is also a preservative. The amounts given are preferred, but the glycerin is optional or can vary. The propylene glycol should be present in the final product in a weight of between 0.5 and 3 percent of the total weight, with the lower amounts preferred if there is substantial glycerin present. To this mixture is added about 1 ml methylparaben and 1/2 ml propylparaben. The mixture is added to the tragacanth carrier and stirred.

Five ml of PABA ("Escalol 507") is then added and stirred until well dissolved. The quantity of PABA given is about two weight percent; up to five weight percent may be used if the product is intended to function as a sunscreen. The methyl- and propylparaben may be present in the range of 0.05 to 0.15 weight percent.

Separately, about one ounce of oil, which is preferably pure shark oil or may be a mixture of shark and mineral or other organic oils, is mixed with an anti-oxidant. A quantity of alpha-tocopherol sufficient to perform as an effective anti-oxidant may be used (I find ¼ gram to be appropriate for pure shark oil), but it is preferred to add at least one of BHA (butylated hydroxyanisole) and BHT (butylated hydroxytoluene) in a range of 0.04 to 0.05 weight percent of the final product (about ⅛ ml. each), to protect the product from rancidity. More than the upper amount indicated for each of BHA and BHT is undesirable as hypersensitivity reactions may occur. In general the weight percentage of oil in the final preparation should be between 6 and 12 percent, with the higher amount preferred, and with the shark oil being from 25% to 100% of the oil. The oil and anti-oxidant are then simply stirred into the carrier preparation for five to ten minutes.

Finally, a small quantity of distilled water, sufficient to achieve the desired consistency, is stirred in until a cream is formed. Any desired fragrance or deodorizer may be added. Final adjustments to the thickness must be made by thinning with water; tragacanth cannot be added at the end of the process to thicken the product.

An excellent suntan lotion may be prepared according to this invention, by using 5 weight percent of PABA and an oil mixture which is fifty percent mineral oil. The mineral oil imparts a somewhat oily sheen to the skin preferred by many sunbathers.

Various modifications of the described invention will occur to those skilled in the art, and it should be understood that the invention includes such modifications as are embraced by, or equivalent to, the invention as claimed herein.

I claim:

1. A cosmetic and moisturizing composition consisting essentially of

| Ingredient | Weight Percent |
| --- | --- |
| Gum Tragacanth | 2.5–4 |
| Ethanol | 0.4–1 |
| Citric Acid | 0–2 |
| Methylparaben | 0.05–0.15 |
| Propylparaben | 0.05–0.15 |
| PABA | 2–5 |
| Oil mixture | 6–12 |
| BHA | 0–0.05 |
| BHT | 0–0.05 |
| Propylene glycol | 0.5–3 |
| Sodium chloride | 0.09–0.11 |
| Water | remainder | in which said oil mixture comprises shark liver oil at 25%–100% by weight, with the remainder being other oils and in which at least one of said BHA or BHT is present in a weight percentage of at least 0.04%.

2. The composition of claim 1 and in which said gum tragacanth is present at 3% by weight and said oil mixture is prsent at 12% by weight and said shark liver oil is essentially 100% of said oil mixture.

3. The composition of claim 1 and in which said PABA is present in a weight percentage of 5% and said shark liver oil is 50% of said oil mixture.

* * * * *